US012558071B2

(12) United States Patent (10) Patent No.: US 12,558,071 B2
Shimomura (45) Date of Patent: Feb. 24, 2026

(54) ULTRASOUND DIAGNOSTIC SYSTEM AND CONTROL METHOD OF ULTRASOUND DIAGNOSTIC SYSTEM

(71) Applicant: FUJIFILM Corporation, Tokyo (JP)

(72) Inventor: Koji Shimomura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 146 days.

(21) Appl. No.: 18/175,510

(22) Filed: Feb. 27, 2023

(65) Prior Publication Data

US 2023/0346355 A1 Nov. 2, 2023

(30) Foreign Application Priority Data

Mar. 30, 2022 (JP) .................................. 2022-056129

(51) Int. Cl.
*A61B 8/00* (2006.01)
*G01P 15/00* (2006.01)

(52) U.S. Cl.
CPC .............. *A61B 8/54* (2013.01); *A61B 8/4488* (2013.01); *A61B 8/56* (2013.01); *G01P 15/00* (2013.01)

(58) Field of Classification Search
CPC ........... A61B 8/54; A61B 8/4488; A61B 8/56; G01P 15/00
See application file for complete search history.

(56) References Cited

U.S. PATENT DOCUMENTS 8,211,132 B2 * 7/2012 Tanaka ........... A61B 17/320068
601/2
2004/0230116 A1 * 11/2004 Cowan ............... A61B 17/2202
600/437

(Continued)

FOREIGN PATENT DOCUMENTS

JP 2001-327497 A 11/2001
JP 2003-190154 A 7/2003
JP 2008-061938 A 3/2008

(Continued)

OTHER PUBLICATIONS

Timothy G. Leighton; Review; What is ultrasound?; Science Direct; Progress in Biophysics and Molecular Biology 93 (2007) pp. 3-83 (Year: 2006).*

(Continued)

*Primary Examiner* — Dixomara Vargas

(74) *Attorney, Agent, or Firm* — Studebaker Brackett PLLC

(57) ABSTRACT

Provided are an ultrasound diagnostic system and a control method of the ultrasound diagnostic system, which enable a user to grasp information regarding a defect occurred in an ultrasound probe in detail.

An ultrasound diagnostic system including: an ultrasound probe having a transducer array; and an apparatus main body that is connected to the ultrasound probe, in which an impact sensor disposed on the ultrasound probe and detecting an impact applied to the ultrasound probe to acquire impact detection information, an ultrasound information acquisition unit that transmits and receives an ultrasound beam from the transducer array and acquires ultrasound information including at least one of a reception signal output from the transducer array or an ultrasound image generated based on the reception signal, in a case where the impact detection information is acquired, and an impact recording memory that records the impact detection information and the ultrasound information are provided.

20 Claims, 5 Drawing Sheets

(56) References Cited

U.S. PATENT DOCUMENTS

| | | | | |
|---|---|---|---|---|
| 2005/0070800 | A1* | 3/2005 | Takahashi | A61B 90/98 600/459 |
| 2007/0136088 | A1* | 6/2007 | Farrel | G06Q 30/016 73/861.18 |
| 2007/0249046 | A1* | 10/2007 | Shields, Jr. | A61H 23/0245 601/2 |
| 2008/0064955 | A1* | 3/2008 | Miyajima | A61B 8/546 600/437 |
| 2011/0083708 | A1* | 4/2011 | Puskas | B08B 3/00 134/113 |
| 2011/0265572 | A1* | 11/2011 | Hoenes | G10K 9/18 73/633 |
| 2013/0194891 | A1 | 8/2013 | Kristoffersen et al. | |
| 2014/0241115 | A1* | 8/2014 | Thattari Kandiyil | G01S 7/52004 367/13 |
| 2015/0164483 | A1* | 6/2015 | Miyajima | A61B 8/14 600/443 |
| 2017/0007851 | A1* | 1/2017 | Da Madice | A61N 7/00 |
| 2017/0089868 | A1* | 3/2017 | Beaty | G01N 29/30 |
| 2017/0176581 | A1* | 6/2017 | Ku | A61B 8/4477 |
| 2017/0258453 | A1* | 9/2017 | Takayama | A61B 8/5261 |
| 2019/0107612 | A1* | 4/2019 | Holl | G01S 15/8913 |
| 2019/0343490 | A1* | 11/2019 | White | A61B 8/5292 |
| 2021/0015516 | A1* | 1/2021 | Kawasaki | A61B 17/320092 |
| 2021/0068782 | A1* | 3/2021 | Caluser | A61B 8/58 |
| 2023/0088350 | A1* | 3/2023 | Iwahashi | G01S 15/8925 600/447 |
| 2024/0007286 | A1* | 1/2024 | Miyamoto | H04L 9/088 |
| 2024/0138810 | A1* | 5/2024 | Huang | A61B 8/06 |

FOREIGN PATENT DOCUMENTS

| | | |
|---|---|---|
| JP | 2013-154169 A | 8/2013 |
| JP | 2021-090651 A | 6/2021 |

OTHER PUBLICATIONS

"Notice of Reasons for Refusal" Office Action issued in JP 2022-056129; mailed by the Japanese Patent Office on Sep. 16, 2025.

* cited by examiner

FIG. 1

FIG. 2
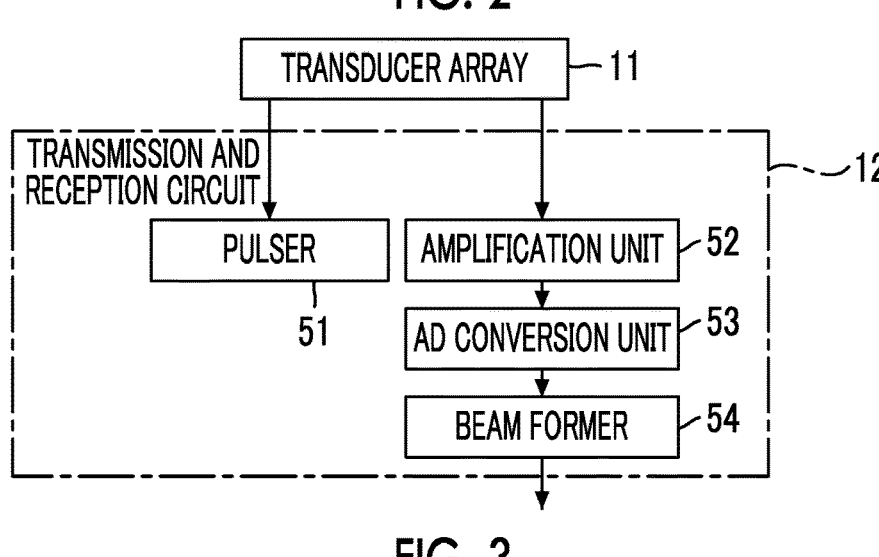
FIG. 3
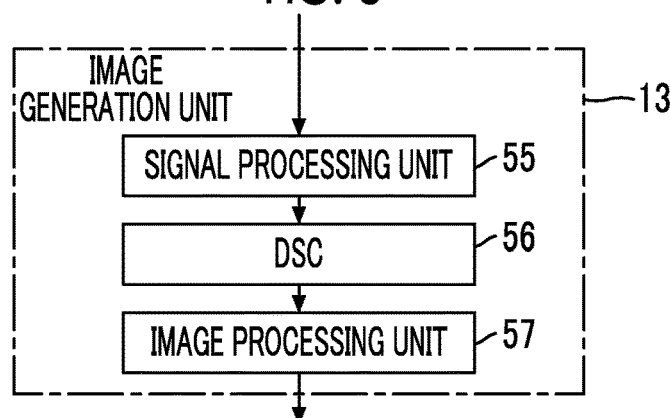
FIG. 4
TRANSDUCER NUMBER

START

S1

DOES IMPACT EXCEED THRESHOLD VALUE?

N

Y

ACQUIRE ULTRASOUND INFORMATION BY TRANSMITTING AND RECEIVING ULTRASOUND WAVE — S2

RECORD IMPACT DETECTION INFORMATION AND ULTRASOUND INFORMATION — S3

ULTRASOUND DIAGNOSTIC SYSTEM AND CONTROL METHOD OF ULTRASOUND DIAGNOSTIC SYSTEM

CROSS-REFERENCE TO RELATED APPLICATIONS

The present application claims priority under 35 U.S.C. § 119 to Japanese Patent Application No. 2022-056129, filed on Mar. 30, 2022. The above application is hereby expressly incorporated by reference, in its entirety, into the present application.

BACKGROUND OF THE INVENTION

1. Field of the Invention

The present invention relates to an ultrasound diagnostic system that detects an impact on an ultrasound probe and a control method of the ultrasound diagnostic system.

2. Description of the Related Art

In the related art, ultrasonography of an inside of a subject has been performed using a so-called ultrasound diagnostic system. In the ultrasonography, a user of the ultrasound diagnostic system performs scanning in a state where a so-called ultrasound probe is in contact with a body surface of the subject and captures an ultrasound image of the inside of the subject. In a case where the ultrasound probe used in this way accidentally falls or the like, defects such as a failure of the ultrasound probe may occur. Therefore, for example, technologies disclosed in JP2021-090651A and JP2013-154169A have been developed so that the user can easily confirm the defect of the ultrasound probe.

JP2021-090651A discloses that log data representing the occurrence of the defect in the ultrasound probe is generated by detecting the fall of the ultrasound probe. In addition, JP2013-154169A discloses that in a state where an ultrasound image is being captured, whether or not uniformity of a transducer array provided in the ultrasound probe is deteriorated is monitored and the result is recorded.

SUMMARY OF THE INVENTION

However, since the log data generated in JP2021-090651A represents the occurrence of the defect in the ultrasound probe, it is difficult for the user of the ultrasound diagnostic system to grasp the detailed location of the defect in the ultrasound probe only by confirming the log data. In addition, in JP2013-154169A, since the uniformity of the transducer array is monitored only in a state where the ultrasound images are continuously captured, for example, in a case where an impact is applied to the ultrasound probe in a state where the ultrasound image is not captured, it is difficult for the user to grasp a cause of the defect of the ultrasound probe. As described above, in JP2021-090651A and JP2013-154169A, it may be difficult for the user to grasp information regarding the defect that occurred in the ultrasound probe in detail.

The present invention has been made to solve the problems of the related art, and an object thereof is to provide an ultrasound diagnostic system in which a user can grasp in detail information regarding a defect that has occurred in an ultrasound probe or a control method of the ultrasound diagnostic system.

In order to achieve the above-described object, the present invention provides an ultrasound diagnostic system comprising: an ultrasound probe having a transducer array; and an apparatus main body that is connected to the ultrasound probe. An impact sensor disposed on the ultrasound probe and detecting an impact applied to the ultrasound probe to acquire impact detection information, an ultrasound information acquisition unit that transmits and receives an ultrasound beam from the transducer array and acquires ultrasound information including at least one of a reception signal output from the transducer array or an ultrasound image generated based on the reception signal, in a case where the impact detection information is acquired by the impact sensor, and an impact recording memory that records the impact detection information acquired by the impact sensor and the ultrasound information acquired by the ultrasound information acquisition unit are provided.

The ultrasound probe can have the ultrasound information acquisition unit and the impact recording memory.

The ultrasound information acquisition unit can automatically acquire the ultrasound information in a case where the impact detection information is acquired by the impact sensor.

In addition, the ultrasound information acquisition unit can also acquire the ultrasound information in a case where the apparatus main body is started.

The ultrasound diagnostic system can comprise an abnormality information acquisition unit that acquires abnormality information including a presence or absence of an abnormality in the transducer array and a content of the abnormality, based on the ultrasound information acquired by the ultrasound information acquisition unit.

The ultrasound diagnostic system can further comprise a notification unit that notifies a user of the abnormality information acquired by the abnormality information acquisition unit.

The ultrasound probe has the abnormality information acquisition unit, and the abnormality information acquired by the abnormality information acquisition unit can be transmitted from the ultrasound probe to the apparatus main body.

The ultrasound probe has a trigger transmission unit that transmits a start trigger signal to the apparatus main body that is in a sleep state and causes the apparatus main body to start, and in a case where the apparatus main body is in the sleep state, in a case where the impact detection information is acquired by the impact sensor, the start trigger signal can be transmitted from the trigger transmission unit to the apparatus main body.

The ultrasound diagnostic system comprises a server that is connected to the apparatus main body, in which the impact detection information acquired by the impact sensor and the abnormality information acquired by the abnormality information acquisition unit can be transmitted to the server via the apparatus main body.

The present invention provides a control method of an ultrasound diagnostic system according to the present invention, the ultrasound diagnostic system including an ultrasound probe having a transducer array and an apparatus main body that is connected to the ultrasound probe, the control method comprising: acquiring impact detection information by detecting an impact applied to the ultrasound probe by an impact sensor disposed on the ultrasound probe, transmitting and receiving an ultrasound beam from the transducer array and acquiring ultrasound information including at least one of a reception signal output from the transducer array or an ultrasound image generated based on the reception signal, in a case where the impact detection information is acquired, and recording the impact detection information and the ultrasound information.

According to the present invention, an ultrasound diagnostic system comprises: an ultrasound probe having a transducer array; and an apparatus main body that is connected to the ultrasound probe. An impact sensor disposed on the ultrasound probe and detecting an impact applied to the ultrasound probe to acquire impact detection information, an ultrasound information acquisition unit that transmits and receives an ultrasound beam from the transducer array and acquires ultrasound information including at least one of a reception signal output from the transducer array or an ultrasound image generated based on the reception signal, in a case where the impact detection information is acquired by the impact sensor, and an impact recording memory that records the impact detection information acquired by the impact sensor and the ultrasound information acquired by the ultrasound information acquisition unit are provided. As a result, a user can grasp information regarding a defect occurred in the ultrasound probe in detail.

BRIEF DESCRIPTION OF THE DRAWINGS

FIG. 1 is a block diagram illustrating a configuration of an ultrasound diagnostic system according to a first embodiment of the present invention.

FIG. 2 is a block diagram illustrating a configuration of a transmission and reception circuit in the first embodiment of the present invention.

FIG. 3 is a block diagram illustrating a configuration of an image generation unit in the first embodiment of the present invention.

FIG. 4 is a diagram schematically illustrating intensities of reception signals acquired by a transducer array in which a part of an ultrasound transducer is damaged.

DESCRIPTION OF THE PREFERRED EMBODIMENTS

Figures 5, 6:
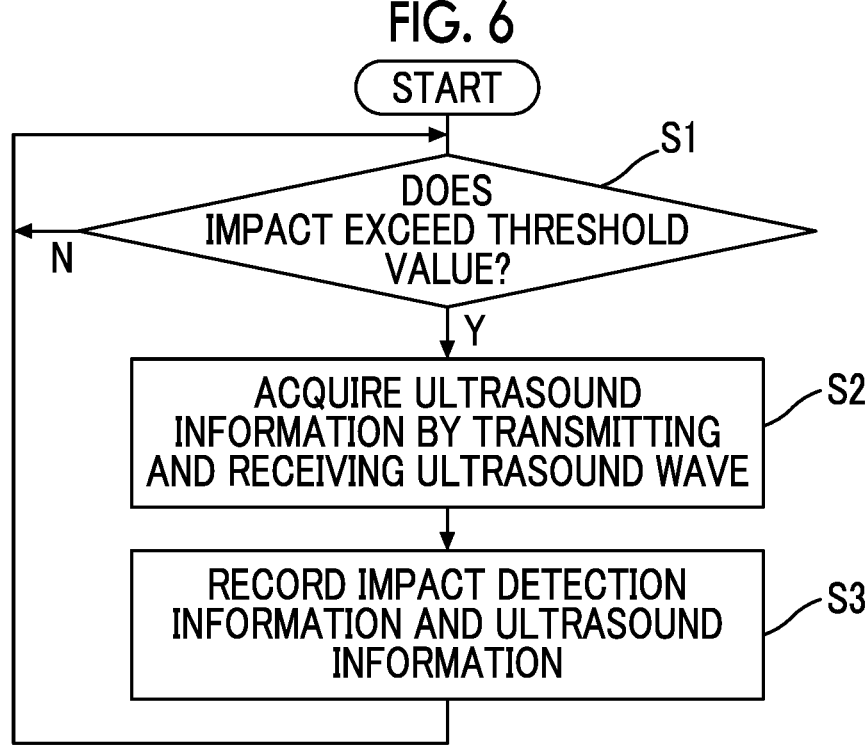
FIG. 5 is a diagram schematically illustrating an example of an ultrasound image in a case of an air radiation state by the transducer array in which a part of the ultrasound transducer is damaged.
FIG. 6 is a flowchart illustrating an operation of the ultrasound diagnostic system according to the first embodiment of the present invention.

Hereinafter, embodiments of the present invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In the present specification, the terms "same" and "identical" include an error range generally allowed in the technical field.

First Embodiment

Figure 1:
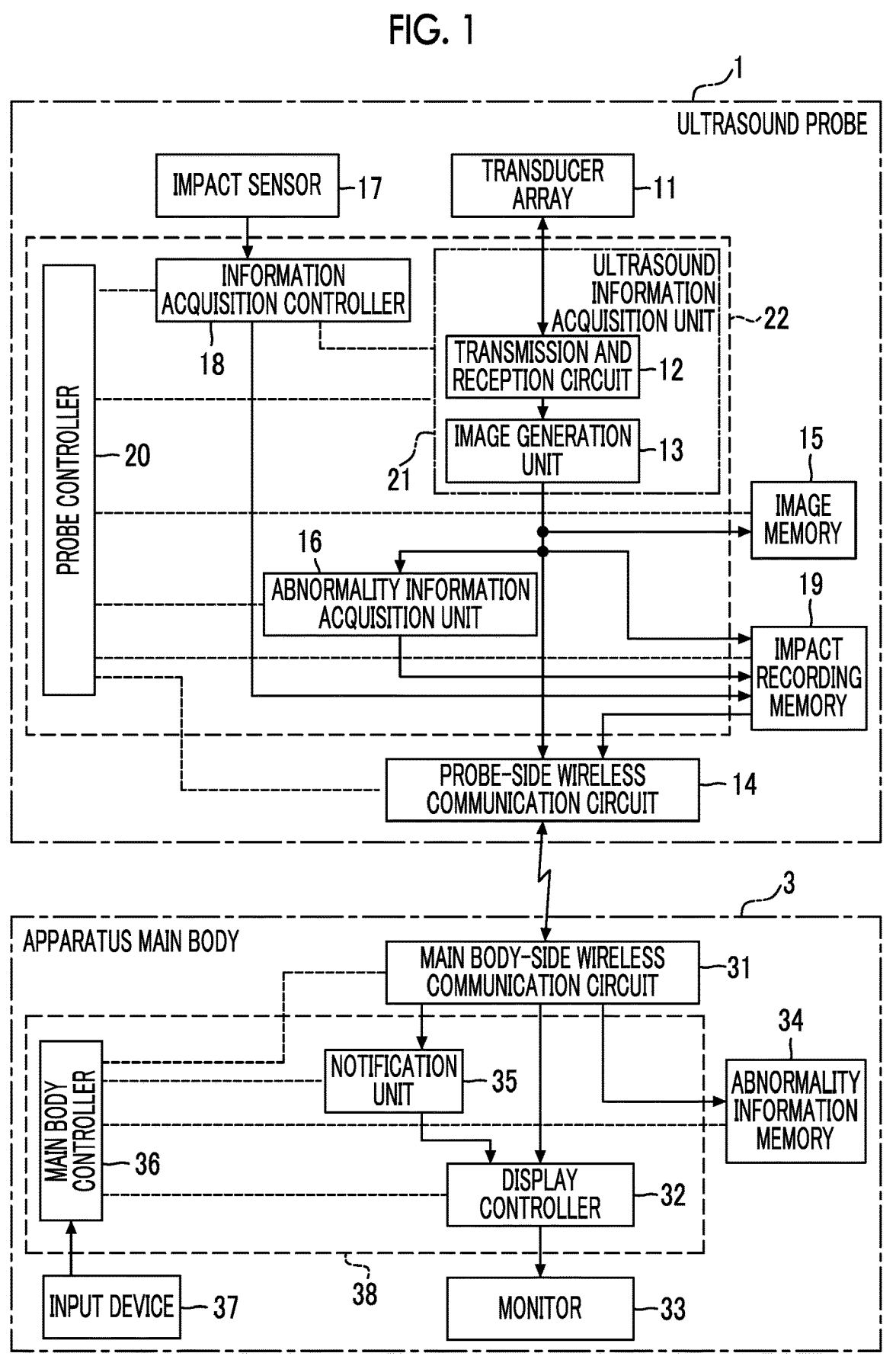

FIG. 1 illustrates a configuration of an ultrasound diagnostic system according to a first embodiment of the present invention. The ultrasound diagnostic system comprises an ultrasound probe 1, and an apparatus main body 3 connected to the ultrasound probe 1 via wireless communication.

The ultrasound probe 1 comprises a transducer array 11. A transmission and reception circuit 12, an image generation unit 13, and a probe-side wireless communication circuit 14 are sequentially connected to the transducer array 11. The transmission and reception circuit 12 and the image generation unit 13 constitute an ultrasound information acquisition unit 21. In addition, an image memory 15 and an abnormality information acquisition unit 16 are connected to the image generation unit 13. In addition, the ultrasound probe 1 comprises an impact sensor 17. An information acquisition controller 18 is connected to the impact sensor 17. The information acquisition controller 18 is connected to the ultrasound information acquisition unit 21. An impact recording memory 19 is connected to the image generation unit 13, the abnormality information acquisition unit 16, and the information acquisition controller 18. The impact recording memory 19 is connected to the probe-side wireless communication circuit 14.

In addition, a probe controller 20 is connected to the ultrasound information acquisition unit 21, the probe-side wireless communication circuit 14, the image memory 15, the abnormality information acquisition unit 16, the information acquisition controller 18, and the impact recording memory 19. In addition, a processor 22 for the ultrasound probe 1 is configured by the ultrasound information acquisition unit 21, the abnormality information acquisition unit 16, the information acquisition controller 18, and the probe controller 20.

The apparatus main body 3 can be configured by a so-called handheld general-purpose apparatus that is easy to carry such as a so-called smartphone or a so-called tablet computer, can be configured by a portable dedicated apparatus that can be carried, and can be configured by a so-called stationary apparatus.

The apparatus main body 3 comprises a main body-side wireless communication circuit 31 that is connected to the probe-side wireless communication circuit 14 of the ultrasound probe 1 via the wireless communication. A display controller 32 and a monitor 33 are sequentially connected to the main body-side wireless communication circuit 31. In addition, an abnormality information memory 34 and a notification unit 35 are connected to the main body-side wireless communication circuit 31. The notification unit 35 is connected to the display controller 32. In addition, a main body controller 36 is connected to the main body-side wireless communication circuit 31, the display controller 32, the abnormality information memory 34, and the notification unit 35. An input device 37 is connected to the main body controller 36. In addition, the display controller 32, the notification unit 35, and the main body controller 36 constitute a processor 38 for the apparatus main body 3.

The transducer array 11 of the ultrasound probe 1 has a plurality of ultrasound transducers arranged in a one-dimensional or two-dimensional manner. According to a drive signal supplied from the transmission and reception circuit 12, each of the ultrasound transducers transmits an ultrasound wave and receives an ultrasound echo from a subject to output a signal based on the ultrasound echo. For example, each ultrasound transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission and reception circuit 12 transmits the ultrasound wave from the transducer array 11 and generates a sound ray signal based on the reception signal acquired by the transducer array 11 under a control of the probe controller 20. As illustrated in FIG. 2, the transmission and reception circuit 12 includes a pulser 51 that is connected to the transducer array 11, and an amplification unit 52, an analog to digital (AD) conversion unit 53, and a beam former 54 that are sequentially connected in series from the transducer array 11.

The pulser 51 includes, for example, a plurality of pulse generators, and the pulser 51 adjusts the amount of delay of each drive signal so that ultrasound waves transmitted from the plurality of ultrasound transducers of the transducer array 11 form an ultrasound beam based on a transmission delay pattern selected according to a control signal from the probe controller 20, and supplies the obtained signals to the plurality of ultrasound transducers. Thus, in a case where a pulsed or continuous-wave voltage is applied to the electrodes of the ultrasound transducers of the transducer array 11, a piezoelectric body expands and contracts to generate pulsed or continuous-wave ultrasound waves from each ultrasound transducer. From the combined wave of these ultrasound waves, an ultrasound beam is formed.

The transmitted ultrasound beam is reflected by a target, for example, a site of the subject, and propagates toward the transducer array 11 of the ultrasound probe 1. The ultrasound echo propagating toward the transducer array 11 in this manner is received by each ultrasound transducer constituting the transducer array 11. In this case, each ultrasound transducer constituting the transducer array 11 expands and contracts by receiving the propagating ultrasound echo to generate a reception signal that is an electric signal, and outputs the reception signal to the amplification unit 52.

The amplification unit 52 amplifies the signals input from each ultrasound transducer constituting the transducer array 11, and transmits the amplified signals to the AD conversion unit 53. The AD conversion unit 53 converts the signal transmitted from the amplification unit 52 into digital reception data. The beam former 54 performs so-called reception focusing processing in which addition is performed by giving delays to respective pieces of the reception data received from the AD conversion unit 53. Through the reception focusing processing, a sound ray signal in which each piece of the reception data converted by the AD conversion unit 53 is phased and added and the focus of the ultrasound echo is narrowed is acquired.

As illustrated in FIG. 3, the image generation unit 13 has a configuration in which a signal processing unit 55, a digital scan converter (DSC) 56, and an image processing unit 57 are sequentially connected in series.

The signal processing unit 55 generates a B-mode image signal, which is tomographic image information regarding tissues inside the subject, by performing, on the sound ray signal received from the transmission and reception circuit 12, correction of the attenuation due to the distance according to the depth of the reflection position of the ultrasound wave using a sound speed value set by the probe controller 20 and then performing envelope detection processing.

The DSC 56 converts the B-mode image signal generated by the signal processing unit 55 into an image signal following a normal television signal scanning method (raster conversion).

The image processing unit 57 performs various kinds of necessary image processing such as gradation processing on the B-mode image signal input from the DSC 56, and then transmits the B-mode image signal to the probe-side wireless communication circuit 14 and the image memory 15. In the following, the B-mode image signal subjected to the image processing by the image processing unit 57 is simply referred to as an ultrasound image.

In addition, the ultrasound information acquisition unit 21 composed of the transmission and reception circuit 12 and the image generation unit 13 transmits the ultrasound information including at least one of the reception signal output from the transducer array 11 or the ultrasound image to the abnormality information acquisition unit 16 and the impact recording memory 19 under the control of the information acquisition controller 18 and the probe controller 20. For example, in a case where the impact is applied to the ultrasound probe 1 by falling the ultrasound probe 1, the ultrasound information includes at least one of the reception signal or the ultrasound image in a so-called air radiation state in which ultrasound wave are radiated from the transducer array 11 in the air.

The image memory 15 stores the ultrasound image generated by the image generation unit 13 under the control of the probe controller 20. Here, as the image memory 15, for example, recording media such as a flash memory, a hard disk drive (HDD), a solid state drive (SSD), a flexible disk (FD), a magneto-optical disk (MO disk), a magnetic tape (MT), a random access memory (RAM), a compact disc (CD), a digital versatile disc (DVD), a secure digital card (SD card), or a universal serial bus memory (USB memory) can be used.

The impact sensor 17 is disposed on the ultrasound probe 1 and detects an impact applied to the ultrasound probe 1 to acquire impact detection information. The impact detection information is information representing that an impact is applied to the ultrasound probe 1, and can include information regarding a value representing the magnitude of the impact and date and time when the impact is applied. In addition, the impact sensor 17 transmits the acquired impact detection information to the information acquisition controller 18. The impact sensor 17 can be configured to include a sensor device capable of detecting an impact, such as a so-called acceleration sensor.

The information acquisition controller 18 stores in advance a predetermined threshold value regarding the magnitude of the impact, and determines whether or not the magnitude of the impact detected by the impact sensor 17 exceeds the threshold value. In addition, the information acquisition controller 18 controls the ultrasound information acquisition unit 21 to transmit and receive an ultrasound beam from the transducer array 11 in a case where the impact detection information including the information of the impact exceeding the threshold value is acquired by the impact sensor 17. In addition, the information acquisition controller 18 transmits the impact detection information received from the impact sensor 17 to the impact recording memory 19.

The abnormality information acquisition unit 16 acquires abnormality information including presence or absence of an abnormality in the transducer array 11 and the content of the abnormality by analyzing the ultrasound information acquired by the ultrasound information acquisition unit 21.

For example, in a case where the abnormality information acquisition unit 16 receives the reception signal as ultrasound information from the ultrasound information acquisition unit 21, the abnormality information acquisition unit 16 determines the presence or absence of the abnormality in the transducer array 11 with reference to a relationship between arrangement numbers (the transducer number) of a plurality of ultrasound transducers constituting the transducer array 11 as shown in FIG. 4 and intensities of the reception signals output from the ultrasound transducers. In the example of FIG. 4, it is shown that the intensity of the reception signal of the ultrasound transducers of the two transducer numbers M1 and M2 is 0, and the intensity of the reception signal of the other ultrasound transducers is a finite value C. In this example, the abnormality information acquisition unit 16 determines that there is an abnormality in the transducer array 11, and can acquire the content that the ultrasound transducers of the two transducer numbers M1 and M2 are out of order as the content of the abnormality.

In addition, the abnormality information acquisition unit 16, for example, analyzes ultrasound image U in a case where the ultrasound image U in an air radiation state as shown in FIG. 5 is received from the ultrasound information acquisition unit 21. In the example of FIG. 5, a multiple reflection image R formed by reflecting ultrasound waves a plurality of times by an acoustic lens or the like (not shown) of the ultrasound probe 1 is obtained, and the multiple reflection image R includes two defective parts N1 and N2. The two defective parts N1 and N2 correspond to different ultrasound transducers, respectively. Therefore, the abnormality information acquisition unit 16 can perform processing for detecting the defective parts N1 and N2 from the ultrasound image U, determine that there is an abnormality in the transducer array 11 in a case where the defective parts N1 and N2 are detected, and acquire, as the content of the abnormality, information that the two ultrasound transducers corresponding to the two defective parts N1 and N2 are out of order.

Here, the abnormality information acquisition unit 16, for example, can detect the defective parts N1 and N2 of the multiple reflection image R by using, for example, a method of a segmentation algorithm such as a so-called binarization method and a so-called diversion method, a method of template matching, a machine learning method described in Csurka et al.: Visual Categorization with Bags of Keypoints, Proc. of ECCV Workshop on Statistical Learning in Computer Vision, pp. 59-74 (2004), or a general image recognition method using deep learning described in Krizhevsk et al.: ImageNet Classification with Deep Convolutional Neural Networks, Advances in Neural Information Processing Systems 25, pp. 1106-1114 (2012).

In addition, not only in a case where a defect such as a failure occurs in the transducer array 11, for example, but also in a case where a defect such that a circuit board (not shown) of the transmission and reception circuit 12 is cracked due to an impact applied to the ultrasound probe 1, an abnormality such as a partial loss of the reception signal and the ultrasound image U may occur. Even in such a case, the abnormality information acquisition unit 16 can determine the presence or absence of the abnormality and determine the content of the abnormality by analyzing the ultrasound information.

The abnormality information acquisition unit 16 transmits the abnormality information acquired in this way to the impact recording memory 19.

The impact recording memory 19 records the impact detection information acquired by the impact sensor 17 and the ultrasound information acquired by the ultrasound information acquisition unit 21 in association with each other. In addition, the impact recording memory 19 can also record the impact detection information and the ultrasound information in association with the abnormality information acquired by the abnormality information acquisition unit 16. In addition, under the control of the probe controller 20, the abnormality information is read out from the impact recording memory 19, and the read abnormality information is transmitted to the probe-side wireless communication circuit 14.

As the impact recording memory 19, for example, recording media such as a flash memory, an HDD, an SSD, an FD, an MO disc, an MT, a RAM, a CD, a DVD, an SD card, or a USB memory can be used.

The probe-side wireless communication circuit 14 is configured by a circuit or the like including an antenna for transmitting and receiving radio waves, and under the control of the probe controller 20, transmits and receives information to and from the main body-side wireless communication circuit 31 of the apparatus main body 3 via the wireless communication. The probe-side wireless communication circuit 14 generates a transmission signal by modulating a carrier based on data transmitted to the main body-side wireless communication circuit 31, for example, and wirelessly transmits the generated transmission signal to the main body-side wireless communication circuit 31.

In this case, as a carrier modulation method, for example, amplitude shift keying (ASK), phase shift keying (PSK), quadrature phase shift keying (QPSK), 16 quadrature amplitude modulation (16 QAM), or the like is used.

The probe controller 20 controls each unit of the ultrasound probe 1 based on a program stored in advance.

Although not illustrated, a battery that supplies power to each unit of the ultrasound probe 1 is built in the ultrasound probe 1.

The processor 22 having the ultrasound information acquisition unit 21, abnormality information acquisition unit 16, the information acquisition controller 18, and the probe controller 20 of the ultrasound probe 1 is configured by a central processing unit (CPU) and a control program for causing the CPU to execute various kinds of processing, but the processor 22 may be configured by using a field programmable gate array (FPGA), a digital signal processor (DSP), an application specific integrated circuit (ASIC), a graphics processing unit (GPU), or other integrated circuits (IC) or may be configured by a combination thereof.

In addition, the ultrasound information acquisition unit 21, the abnormality information acquisition unit 16, the information acquisition controller 18, and the probe controller 20 of the processor 22 can be partially or wholly integrated into one CPU or the like.

The main body-side wireless communication circuit 31 of the apparatus main body 3 is configured by a circuit or the like including an antenna for transmitting and receiving radio waves, and under the control of the main body controller 36, transmits and receives information to and from the probe-side wireless communication circuit 14 of the ultrasound probe 1 via the wireless communication. The main body-side wireless communication circuit 31 generates a transmission signal by modulating a carrier based on data transmitted to the probe-side wireless communication circuit 14, for example, and wirelessly transmits the generated transmission signal to the probe-side wireless communication circuit 14.

The display controller 32 performs predetermined processing on the ultrasound image transmitted from the probe-side wireless communication circuit 14 to the main body-side wireless communication circuit 31 and displays it on the monitor 33 under the control of the main body controller 36.

The monitor 33 performs various kinds of display under the control of the display controller 32. For example, the monitor 33 can include a display device such as a liquid crystal display (LCD) or an organic electroluminescence (EL) display.

The abnormality information memory 34 records the abnormality information transmitted from the probe-side wireless communication circuit 14 to the main body-side wireless communication circuit 31. As the impact recording memory 19, for example, recording media such as a flash memory, an HDD, an SSD, an FD, an MO disc, an MT, a RAM, a CD, a DVD, an SD card, or a USB memory can be used. The abnormality information recorded in the abnormality information memory 34 can be easily confirmed by, for example, a user of the ultrasound diagnostic system. By confirming the abnormality information in this way, the user can grasp the presence or absence of the abnormality in the ultrasound probe 1 and the location where the abnormality has occurred in the ultrasound probe 1 in detail.

The notification unit 35 notifies the user of the abnormality information transmitted from the probe-side wireless communication circuit 14 to the main body-side wireless communication circuit 31. The notification unit 35 can notify the abnormality information by displaying a message on the monitor 33, for example. As a result, the user can grasp in detail and easily the presence or absence of the abnormality in the ultrasound probe 1 and the location where the abnormality has occurred in the ultrasound probe 1.

The main body controller 36 controls each unit of the apparatus main body 3 based on a program stored in advance.

The input device 37 receives an input operation of the user and transmits input information to the main body controller 36. The input device 37 is configured by, for example, a device for a user to perform an input operation, such as a keyboard, a mouse, a trackball, a touchpad, a touch panel, or the like.

The processor 38 including the display controller 32, the notification unit 35, and the main body controller 36 of the apparatus main body 3 is configured with a CPU and a control program for causing the CPU to perform various processing. On the other hand, the processor 38 may be configured using FPGA, DSP, ASIC, GPU, or other ICs, or may be configured by a combination thereof.

In addition, the display controller 32, the notification unit 35, and the main body controller 36 of the processor 38 may be partially or wholly integrated into, for example, one CPU.

Next, an example of the operation of the ultrasound diagnostic system according to the first embodiment will be described using the flowchart illustrated in FIG. 6.

First, in step S1, the information acquisition controller 18 receives the impact detection information from the impact sensor 17 and determines whether or not the magnitude of the impact detected by the impact sensor 17 exceeds a predetermined threshold value. In a case where the magnitude of the impact detected by the impact sensor 17 is equal to or less than the threshold value, the processing of step S1 is performed again. In a case where the magnitude of the impact detected by the impact sensor 17 exceeds the threshold value, the processing proceeds to step S2.

In step S2, the information acquisition controller 18 controls the ultrasound information acquisition unit 21 so as to automatically transmit and receive ultrasound waves in the transducer array 11. As a result, the ultrasound information acquisition unit 21 acquires ultrasound information in an air radiation state as shown in FIGS. 4 and 5, for example. Thus, the ultrasound information immediately after a large impact is applied to the ultrasound probe 1 is acquired.

In a case where any one of the plurality of ultrasound transducers constituting the transducer array 11 is out of order due to the impact applied to the ultrasound probe 1, for example, the signal corresponding to the transducer numbers M1 and M2 shown in FIG. 4 or as the defective parts N1 and N2 of the multiple reflection image R shown in FIG. 5, the signal corresponding to the failed ultrasound transducer in the ultrasound information may be lost. In addition, even in a case there is a defect such as a case of occurring a crack in a circuit board (not shown) of the transmission and reception circuit 12, a loss of the signal may occur. For example, the user can grasp that the ultrasound probe 1 has a defect by confirming the abnormality ultrasound information including the defective part.

In step S3, under the control of the probe controller 20, the impact recording memory 19 records the impact detection information acquired by the impact sensor 17 in step S1 and the ultrasound information acquired by the ultrasound information acquisition unit 21 in step S2 in association with each other. By confirming the impact detection information and the ultrasound information recorded in the impact recording memory 19, the user can grasp that the defect such as a failure has occurred in the transducer array 11 due to the impact applied to the ultrasound probe 1 and the location where the defect has occurred in the ultrasound probe 1 in detail.

In this way, in a case where the processing of step S3 is completed, the processing returns to step S1, and thereafter, the processing of steps S1 to S3 is repeated to acquire the ultrasound information and record the impact detection information and the ultrasound information every time the impact sensor 17 detects an impact having a magnitude exceeding a predetermined threshold value.

Here, the ultrasound probe 1 incorporates a battery (not shown) that supplies power to each unit of the ultrasound probe 1, and the operations of steps S1 to S3 are performed in the ultrasound probe 1 independently of the apparatus main body 3. That is, in a case where the processing of steps S1 to S3 are performed, the apparatus main body 3 may or may not be started. A state in which the apparatus main body 3 is started means a state in which each unit of the apparatus main body 3 is operating. In addition, a state in which the apparatus main body 3 is not started includes a state in which the power of the apparatus main body 3 is turned off and the entire operation of the apparatus main body 3 is stopped, and a so-called sleep state in which the operation of a part of the apparatus main body 3 is stopped excluding wireless communication with the ultrasound probe 1.

In addition, the ultrasound probe 1 has, as an operation state, a starting state in which each unit of the ultrasound probe 1 is operating, a sleep state in which at least the impact sensor 17 and the probe controller 20 are operating, and a power-off state in which the entire operation of the ultrasound probe 1 is stopped. The ultrasound probe 1 may be in the starting state or the sleep state in a case where the operations of step S1 to step S3 are performed. In a case where the impact sensor 17 detects an impact from the outside in a case where the ultrasound probe 1 is in the sleep state, for example, under the control of the probe controller 20, each unit of the ultrasound probe 1 operates in sequence so that the operations of step S1 to step S3 are performed.

From the above, according to the ultrasound diagnostic system according to the first embodiment of the present invention, the impact sensor 17 acquires the impact detection information in a case where an impact is applied to the ultrasound probe 1, and the ultrasound information acquisition unit 21 acquires the ultrasound information based on the impact detection information. Since the impact detection information and the ultrasound information are associated with each other and are recorded in the impact recording memory 19, the user can easily and in detail grasp information regarding the defect including that the defect has occurred in the ultrasound probe 1 and the location where the defect has occurred in the ultrasound probe 1.

Although it is described that regardless of whether or not the apparatus main body 3 is started, in a case where the magnitude of the impact detected by the impact sensor 17 exceeds the predetermined threshold value, the ultrasound information is acquired automatically by the ultrasound information acquisition unit 21, for example, the ultrasound information can be acquired at the timing when the apparatus main body 3 is started. In this case, for example, the information acquisition controller 18 can control the ultrasound information acquisition unit 21 so as to automatically transmit and receive ultrasound waves in the transducer array 11 in a case where the impact detection information representing that the impact having the magnitude exceeding the predetermined threshold value is applied to the ultrasound probe 1 is received from the impact sensor 17 and the apparatus main body 3 is started. Even in this case, since the user can confirm the impact detection information recorded in the impact recording memory 19, the user can grasp the information regarding the defect that has occurred in the ultrasound probe 1 together with the ultrasound information in detail.

In addition, in a case where the apparatus main body 3 is started, in the flowchart shown in FIG. 6, immediately after the processing of step S3 is performed, the ultrasound diagnostic system can perform processing to wirelessly transmit abnormality information that is acquired by the abnormality information acquisition unit 16 and is recorded in the impact recording memory 19 from the probe-side wireless communication circuit 14 to the main body-side wireless communication circuit 31, processing to record the abnormality information by the abnormality information memory 34, and processing to notify the user of the abnormality information by the notification unit 35. By recording the abnormality information in the abnormality information memory 34, the user can easily confirm the abnormality information from the abnormality information memory 34. In addition, the notification unit 35 notifies the user of the abnormality information, so that the user can easily confirm the abnormality information on the spot, for example, by confirming the notification message displayed on the monitor 33.

In addition, in a case where the apparatus main body 3 is not started in a case where the impact sensor 17 detects the impact having the magnitude exceeding the predetermined threshold value, for example, the probe controller 20 can subsequently read out the abnormality information from the impact recording memory 19 at the timing when the apparatus main body 3 is started, and wirelessly transmit the read abnormality information from the probe-side wireless communication circuit 14 to the main body-side wireless communication circuit 31. As a result, the abnormality information is recorded in the abnormality information memory 34 without omission each time the apparatus main body 3 is started, so that the user can confirm the abnormality information in detail without omission.

Second Embodiment

Even the apparatus main body 3 is in a sleep state, in a case where an impact having a magnitude exceeding the predetermined threshold value is detected by the impact sensor 17, the apparatus main body 3 can be automatically started to wirelessly transmit the abnormality information from the probe-side wireless communication circuit 14 to the main body-side wireless communication circuit 31.

Figure 7:
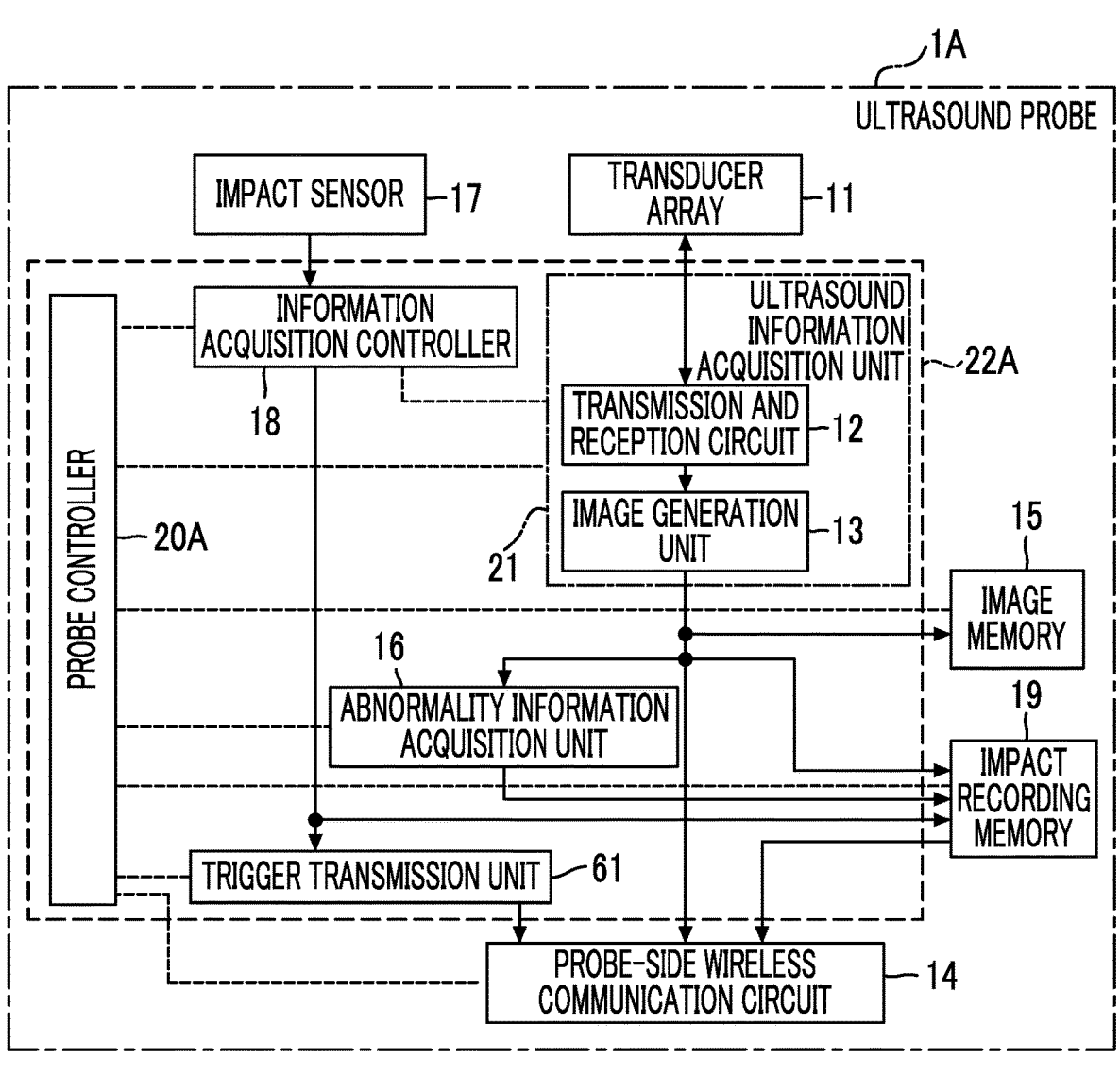
FIG. 7 is a block diagram illustrating a configuration of an ultrasound diagnostic system according to a second embodiment of the present invention.

The ultrasound diagnostic system according to the second embodiment comprises an ultrasound probe 1A shown in FIG. 7 instead of the ultrasound probe 1 in the ultrasound diagnostic system according to the first embodiment shown in FIG. 1. In the ultrasound probe 1A, as compared with the ultrasound probe 1 according to the first embodiment, a trigger transmission unit 61 is added and a probe controller 20A is included instead of the probe controller 20.

In the ultrasound probe 1A, the trigger transmission unit 61 is connected to the information acquisition controller 18. The trigger transmission unit 61 is connected to the probe-side wireless communication circuit 14 and the probe controller 20A. In addition, the processor 22A for the ultrasound probe 1A is configured by the ultrasound information acquisition unit 21, the abnormality information acquisition unit 16, the information acquisition controller 18, the probe controller 20A, and the trigger transmission unit 61.

The information acquisition controller 18 transmits an impact detection signal to the trigger transmission unit 61 in a case where an impact detection signal representing that an impact having a magnitude exceeding the predetermined threshold value is detected is acquired by the impact sensor 17.

In a case of receiving the impact detection signal from the information acquisition controller 18, the trigger transmission unit 61 transmits a start trigger signal to the apparatus main body 3 which is in a sleep state via the probe-side wireless communication circuit 14 to start the apparatus main body 3.

In a case where the apparatus main body 3 is started in this way, the abnormality information is read out from the impact recording memory 19 under the control of the probe controller 20, and the abnormality information is wirelessly transmitted from the probe-side wireless communication circuit 14 to the main body-side wireless communication circuit 31. The abnormality information received by the main body-side wireless communication circuit 31 is recorded in the abnormality information memory 34. In addition, the abnormality information received by the main body-side wireless communication circuit 31 can also be notified to the user by the notification unit 35.

As described above, according to the ultrasound diagnostic system according to the second embodiment, even in a case where the apparatus main body 3 is in a sleep state, since the apparatus main body 3 is started every time the impact sensor 17 detects a large impact, and the abnormality information is recorded in the abnormality information memory 34 at any time, the abnormality information is recorded in the abnormality information memory 34 without omission and the user can confirm the abnormality information in detail without omission. In addition, every time the impact sensor 17 detects a large impact, abnormality information is notified, so that, for example, in a case where the ultrasound diagnostic system is in the vicinity of the user, the user can immediately grasp that an abnormality has occurred in the ultrasound probe 1A.

Third Embodiment

Although it is described that the abnormality information memory 34 is included in the apparatus main body 3, for example, a server located at a remote location for the ultrasound probe 1 and the apparatus main body 3 can also be provided with the abnormality information memory 34 so that a worker or the like who is at a remote location for the ultrasound probe 1 and the apparatus main body 3 and who performs maintenance and inspection can confirm the abnormality information of the ultrasound probe 1.

Figure 8:
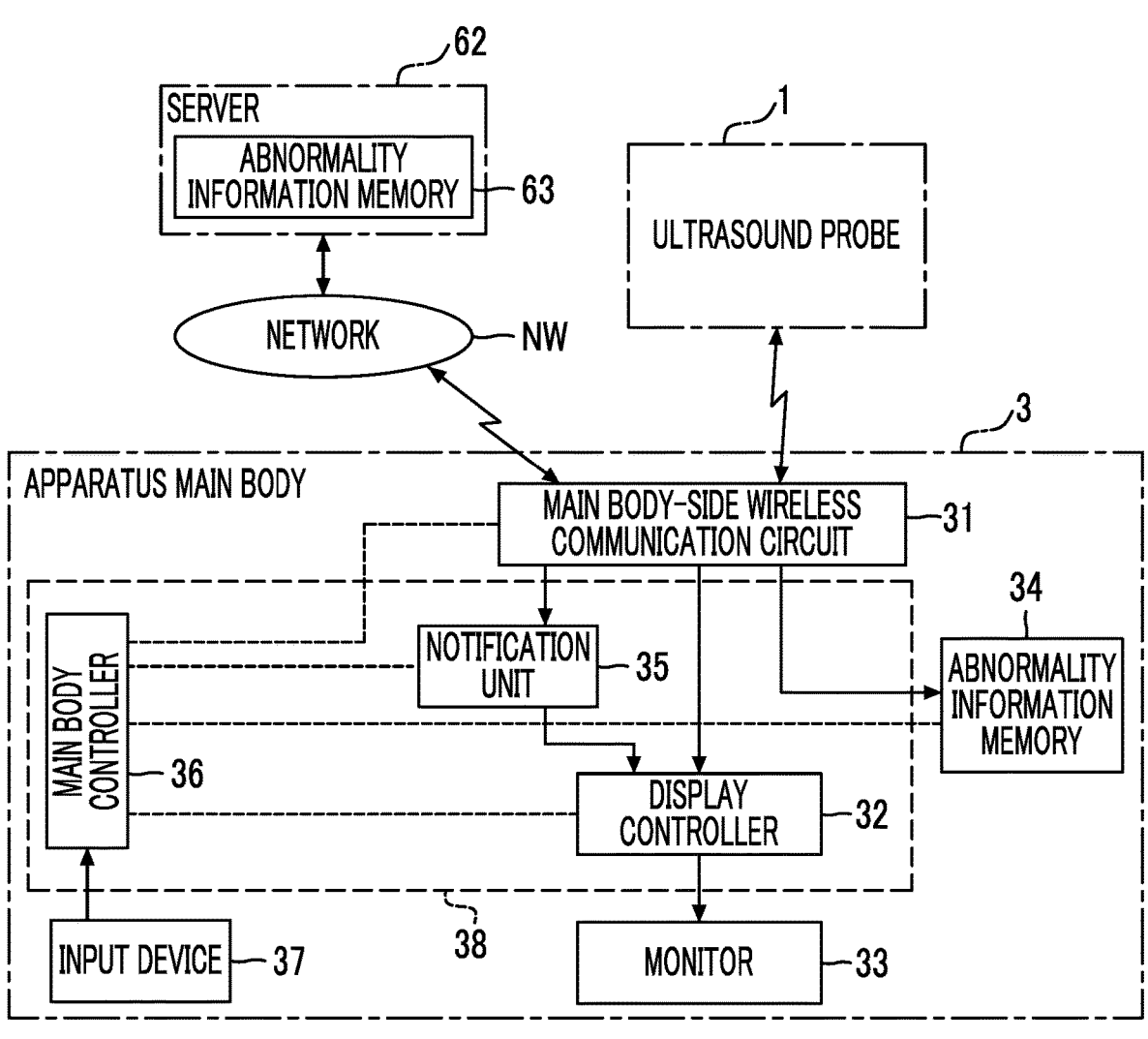
FIG. 8 is a block diagram illustrating a configuration of an ultrasound diagnostic system according to a third embodiment of the present invention.

FIG. 8 illustrates a configuration of an ultrasound diagnostic system according to the third embodiment. The ultrasound diagnostic system according to the third embodiment is the ultrasound diagnostic system according to the first embodiment shown in FIG. 1, in which a server 62 connected to the apparatus main body 3 via a network NW is added.

The main body-side wireless communication circuit 31 of the apparatus main body 3 is connected to the network NW via the wireless communication.

The server 62 is configured by, for example, a computer that can be connected to the network NW and is located at a remote location for the ultrasound probe 1 and the apparatus main body 3. In addition, the server 62 is connected to the main body-side wireless communication circuit 31 of the apparatus main body 3 via the network NW. In addition, the server 62 comprises an abnormality information memory 63.

The abnormality information memory 63 records the abnormality information that is acquired by the abnormality information acquisition unit 16 of the ultrasound probe 1 and that is transmitted from the ultrasound probe 1 to the server 62 via the apparatus main body 3 and the network NW. As the abnormality information memory 63, for example, recording media such as a flash memory, an HDD, an SSD, an FD, an MO disc, an MT, a RAM, a CD, a DVD, an SD card, or a USB memory can be used.

From the above, according to the ultrasound diagnostic system according to the third embodiment, since the abnormality information acquired by the abnormality information acquisition unit 16 of the ultrasound probe 1 is recorded in the abnormality information memory 63 of the server 62 via the apparatus main body 3 and the network NW, for example, the worker who is at a remote location for the ultrasound probe 1 and the apparatus main body 3 can easily confirm the abnormality information of the ultrasound probe 1, and it is possible to take appropriate measures such as inspection or repair of the ultrasound probe 1.

Although it is described that the abnormality information acquired by the abnormality information acquisition unit 16 is recorded in the abnormality information memory 63 of the server 62, impact detection information representing that an impact having a magnitude exceeding the predetermined threshold value is applied to the ultrasound probe 1, and the ultrasound information acquired by the ultrasound information acquisition unit 21 in response to an impact having a magnitude exceeding the predetermined threshold value being applied to the ultrasound probe 1 are transmitted from the ultrasound probe 1 to the server 62 via the apparatus main body 3 and the network NW, and can also be recorded in the abnormality information memory 63. Accordingly, a worker who is at a remote location for the ultrasound probe 1 and the apparatus main body 3 can grasp the abnormality occurred in the ultrasound probe 1 in more detail by confirming the impact detection information and the ultrasound information.

In addition, it is described that the abnormality information acquired by the abnormality information acquisition unit 16 of the ultrasound probe 1 is transmitted to the server 62 via the apparatus main body 3 and the network NW, but the ultrasound diagnostic system can also transmit the abnormality information from the ultrasound probe 1 to the server 62 via the network NW without going through the apparatus main body 3. In this case, the probe-side wireless communication circuit 14 of the ultrasound probe 1 is connected to the network NW. In this case, the impact detection information and the ultrasound information can also be transmitted from the ultrasound probe 1 to the server 62 via the network NW.

EXPLANATION OF REFERENCES

1, 1A: ultrasound probe
3: apparatus main body
11: transducer array
12: transmission and reception circuit
13: image generation unit
14: probe-side wireless communication circuit
15: image memory
16: abnormality information acquisition unit
17: impact sensor
18: information acquisition controller
19: impact recording memory
20, 20A: probe controller
21: ultrasound information acquisition unit
22, 22A: processor
31: main body-side wireless communication circuit
32: display controller
33: monitor
34, 63: abnormality information memory
35: notification unit
36: main body controller
37: input device
51: pulser
52: amplification unit
53: AD conversion unit
54: beam former
55: signal processing unit
56: DSC
57: image processing unit
61: trigger transmission unit
62: server
C: value
M1, M2: transducer number
N1, N2: defective part
R multiple reflection image
U: ultrasound image

What is claimed is:

1. An ultrasound diagnostic system including an ultrasound probe having a transducer array composed by a plurality of ultrasound transducers and an acoustic lens covering the transducer array, and an ultrasound diagnostic apparatus that is connected to and interactively communicating with the ultrasound probe, comprising:

an impact sensing device disposed on the ultrasound probe configured to detect a physical impact from outside the ultrasound probe applied to the ultrasound probe, to acquire impact detection information, a processor configured to determine whether a magnitude of the physical impact exceeds a predetermined threshold value based on the impact detection information, upon determining that the magnitude of the physical impact exceeds the predetermined threshold value, transmit ultrasound waves from the transducer array automatically, receive an ultrasound echo that occurred by reflections of the ultrasound waves at the acoustic lens, and acquire ultrasound information including at least one of a reception signal output from the transducer array that received the ultrasound echo or an ultrasound image generated based on the reception signal, and an impact recording memory configured to record the impact detection information acquired by the impact sensing device and the ultrasound information acquired by the processor, wherein the reception signal and the ultrasound image represent a multiple reflection image formed by reflecting the ultrasound waves a plurality of times by the acoustic lens, and the multiple reflection image includes a defective part corresponding to an ultrasound transducer that is out of order due to the physical impact.

2. The ultrasound diagnostic system according to claim 1, wherein the ultrasound probe includes the processor and the impact recording memory.

3. The ultrasound diagnostic system according to claim 1, wherein the processor is further configured to automatically acquire the ultrasound information once the impact detection information is acquired by the impact sensing device.

4. The ultrasound diagnostic system according to claim 2, wherein the processor is further configured to automatically acquire the ultrasound information once the impact detection information is acquired by the impact sensing device.

5. The ultrasound diagnostic system according to claim 1, wherein the processor is further configured to automatically acquire the ultrasound information when the ultrasound diagnostic apparatus is started in a state that the impact detection information has been acquired by the impact sensing device.

6. The ultrasound diagnostic system according to claim 2, wherein the processor is further configured to automatically acquire the ultrasound information when the ultrasound diagnostic apparatus is started in a state that the impact detection information has been acquired by the impact sensing device.

7. The ultrasound diagnostic system according to claim 1, wherein the processor is further configured to acquire abnormality information including a presence or absence of a failure in the transducer array due to the physical impact and a content of the failure, based on the ultrasound information.

8. The ultrasound diagnostic system according to claim 2, wherein the processor is further configured to acquire abnormality information including a presence or absence of a failure in the transducer array due to the physical impact and a content of the failure, based on the ultrasound information.

9. The ultrasound diagnostic system according to claim 3, wherein the processor is further configured to acquire abnormality information including a presence or absence of a failure in the transducer array due to the physical impact and a content of the failure, based on the ultrasound information.

10. The ultrasound diagnostic system according to claim 4, wherein the processor is further configured to acquire abnormality information including a presence or absence of a failure in the transducer array due to the physical impact and a content of the failure, based on the ultrasound information.

11. The ultrasound diagnostic system according to claim 7, wherein the processor is further configured to notify a user of the abnormality information.

12. The ultrasound diagnostic system according to claim 8, wherein the processor is further configured to notify a user of the abnormality information.

13. The ultrasound diagnostic system according to claim 9, wherein the processor is further configured to notify a user of the abnormality information.

14. The ultrasound diagnostic system according to claim 10, wherein the processor is further configured to notify a user of the abnormality information.

15. The ultrasound diagnostic system according to claim 7, wherein the abnormality information acquired by the processor is transmitted from the ultrasound probe to the ultrasound diagnostic apparatus.

16. The ultrasound diagnostic system according to claim 8, wherein the abnormality information acquired by the processor is transmitted from the ultrasound probe to the ultrasound diagnostic apparatus.

17. The ultrasound diagnostic system according to claim 11, wherein the abnormality information acquired by the processor is transmitted from the ultrasound probe to the ultrasound diagnostic apparatus.

18. The ultrasound diagnostic system according to claim 15, wherein the processor is further configured to cause the ultrasound diagnostic apparatus to start by transmitting a start trigger to the ultrasound diagnostic apparatus when the impact detection information is acquired by the impact sensing device while the ultrasound diagnostic apparatus is in a sleep state.

19. The ultrasound diagnostic system according to claim 7, further comprising:

a server that is connected to the ultrasound diagnostic apparatus, wherein the impact detection information acquired by the impact sensing device and the abnormality information acquired by the processor are transmitted to the server via the ultrasound diagnostic apparatus.

20. A control method of an ultrasound diagnostic system including an ultrasound probe having a transducer array composed by a plurality of ultrasound transducers and an acoustic lens covering the transducer array, and an ultrasound diagnostic apparatus that is connected to and interactively communicating with the ultrasound probe, the control method comprising:

acquiring impact detection information by detecting a physical impact from outside of the ultrasound probe applied to the ultrasound probe by an impact sensor disposed on the ultrasound probe, determining whether a magnitude of the physical impact exceeds a predetermined threshold value based on the impact detection information, upon determining that the magnitude of the physical impact exceeds the predetermined threshold value, transmitting an ultrasound waves from the transducer array automatically, receiving an ultrasound echo that occurred by reflections of the ultrasound waves at the acoustic lens, and acquiring ultrasound information including at least one of a reception signal output from the transducer array that received the ultrasound echo or an ultrasound image generated based on the reception signal, and recording the impact detection information and the ultrasound information, wherein the reception signal and the ultrasound image represent a multiple reflection image formed by reflecting the ultrasound waves a plurality of times by the acoustic lens, and the multiple reflection image includes a defective part corresponding to an ultrasound transducer that is out of order due to the physical impact.

\* \* \* \* \*